US012755592B2

(12) United States Patent
Cha

(10) Patent No.: US 12,755,592 B2
(45) Date of Patent: Oct. 6, 2026

(54) MANAGING SERVER, MANAGING METHOD AND COMPUTER PROGRAM FOR OPERATING BIOMETRIC INFORMATION-BASED ACCESS MANAGEMENT SYSTEM

(71) Applicant: Edward Cha, Seoul (KR)

(72) Inventor: Edward Cha, Seoul (KR)

( * ) Notice: Subject to any disclaimer, the term of this patent is extended or adjusted under 35 U.S.C. 154(b) by 3 days.

(21) Appl. No.: 19/082,181

(22) Filed: Mar. 18, 2025

(65) Prior Publication Data

US 2025/0218241 A1 Jul. 3, 2025

Related U.S. Application Data

(63) Continuation-in-part of application No. 17/860,086, filed on Jul. 7, 2022, now abandoned.

(51) Int. Cl.

| | |
|---|---|
| ***G07C 9/25*** | (2020.01) |
| ***A61B 5/00*** | (2006.01) |
| ***A61B 5/01*** | (2006.01) |
| ***G06F 21/32*** | (2013.01) |

(52) U.S. Cl.

CPC .............. *G07C 9/25* (2020.01); *A61B 5/0022* (2013.01); *A61B 5/01* (2013.01); *A61B 5/6803* (2013.01); *G06F 21/32* (2013.01)

(58) Field of Classification Search

CPC ........ G07C 9/25; G07C 9/28; G07C 2209/14; A61B 5/0022; A61B 5/01

See application file for complete search history.

(56) References Cited

U.S. PATENT DOCUMENTS

| | | | | |
|---|---|---|---|---|
| 2021/0304537 | A1* | 9/2021 | Reed | G06F 18/22 |
| 2021/0339058 | A1* | 11/2021 | Connor | A62B 18/08 |
| 2024/0005432 | A1* | 1/2024 | Aman | G06Q 50/22 |
| 2025/0049393 | A1* | 2/2025 | Hester | A61B 5/02438 |

* cited by examiner

*Primary Examiner* — Nabil H Syed
(74) *Attorney, Agent, or Firm* — Nicholas Park

(57) ABSTRACT

The present invention relates to an access management system that determines whether to approve a user's authentication request for a management space based on biometric data measured by multiple smart wearable devices. The system includes a smart mask with a temperature sensor, a fan system for air circulation, and an external indicator for fan status, as well as a wireless headset with an additional temperature sensor. The management server verifies authentication conditions using biometric data and public database authentication data. The fan system dynamically adjusts airflow based on the user's biometric and environmental data, while the external indicator provides real-time feedback. The system enhances accuracy by incorporating body temperature correction from the wireless headset and calculating a comprehensive health score. By eliminating manual QR code scanning and improving body temperature measurement accuracy, the invention enhances authentication efficiency, user convenience, and access security while enabling continuous biometric monitoring.

6 Claims, 13 Drawing Sheets

MANAGING SERVER, MANAGING METHOD AND COMPUTER PROGRAM FOR OPERATING BIOMETRIC INFORMATION-BASED ACCESS MANAGEMENT SYSTEM

CROSS-REFERENCE TO RELATED APPLICATION

This application is a Continuation-in-Part Application of U.S. patent application Ser. No. 17/860,086, filed on Jul. 7, 2022, the disclosure of which is incorporated herein by reference in its entirety.

BACKGROUND

Technical Field

The present disclosure of the following description relates to managing server, managing method and a computer program for operating a biometric information-based access management system, and more particularly, to an access management system determining whether to approve the user's authentication request for the management space based on biometric data measured by a wearable device such as a smart mask.

Background Art

Due to the epidemic of infectious diseases, it may be required to control and manage people's access to a management space that requires access management, such as a restaurant. In the past, access management was performed by checking the QR code and checking the body temperature to identify the movement of infected people and check whether people were vaccinated. But there is a problem that the QR code check causes inconvenience and the body temperature test has low accuracy.

SUMMARY OF THE INVENTION

Technical Problem

An object of the present disclosure is to provide a method for operating an access management system based on biometric data measured by a wearable device directly worn on the user's body, in order to solve the problem that the QR code check causes inconvenience and the body temperature test has low accuracy.

Technical Solution

In accordance with the present invention, a management server for operating a biometric information-based access management system may include a memory configured to save commands; and a processor configured to: receive, from a user terminal, an authentication request for a management space of an access management system and a user's biometric data collected by a smart mask; determine whether the user satisfies an authentication condition of the management space based on the biometric data and a user's authentication data retrieved from a public database; send an approval message for the authentication request and periodic data requests to the user terminal when the authentication condition is satisfied; periodically receive the position of the smart mask and subsequent biometric data of the user generated in response to the periodic data requests from the user terminal; and send an authentication failure message to the user terminal if the authentication condition is not satisfied based on the subsequent biometric data and the user's subsequent authentication data periodically received while the smart mask is in the management space.

In accordance with the present invention, a management method for operating a biometric information-based access management system which is performed by a processor executing commands saved in the memory, the method may include receiving, from a user terminal, an authentication request for a management space of an access management system and a user's biometric data collected by a smart mask; determining whether the user satisfies an authentication condition of the management space based on the biometric data and a user's authentication data retrieved from a public database; sending an approval message for the authentication request and periodic data requests to the user terminal when the authentication condition is satisfied; periodically receiving the position of the smart mask and subsequent biometric data of the user generated in response to the periodic data requests from the user terminal; and sending an authentication failure message to the user terminal if the authentication condition is not satisfied based on the subsequent biometric data and the user's subsequent authentication data periodically received while the smart mask is in the management space.

In accordance with the present invention, in a computer program including commands saved in a computer-readable storage medium to implement a management method for operating a biometric information-based access management system, the commands cause a processor to: receive, from a user terminal, an authentication request for a management space of an access management system and a user's biometric data collected by a smart mask; determine whether the user satisfies an authentication condition of the management space based on the biometric data and a user's authentication data retrieved from a public database; send an approval message for the authentication request and periodic data requests to the user terminal when the authentication condition is satisfied; periodically receive the position of the smart mask and subsequent biometric data of the user generated in response to the periodic data requests from the user terminal; and send an authentication failure message to the user terminal if the authentication conditions is not satisfied based on the subsequent biometric data and the user's subsequent authentication data periodically received while the smart mask is in the management space.

DETAILED DESCRIPTION

Figure 1:
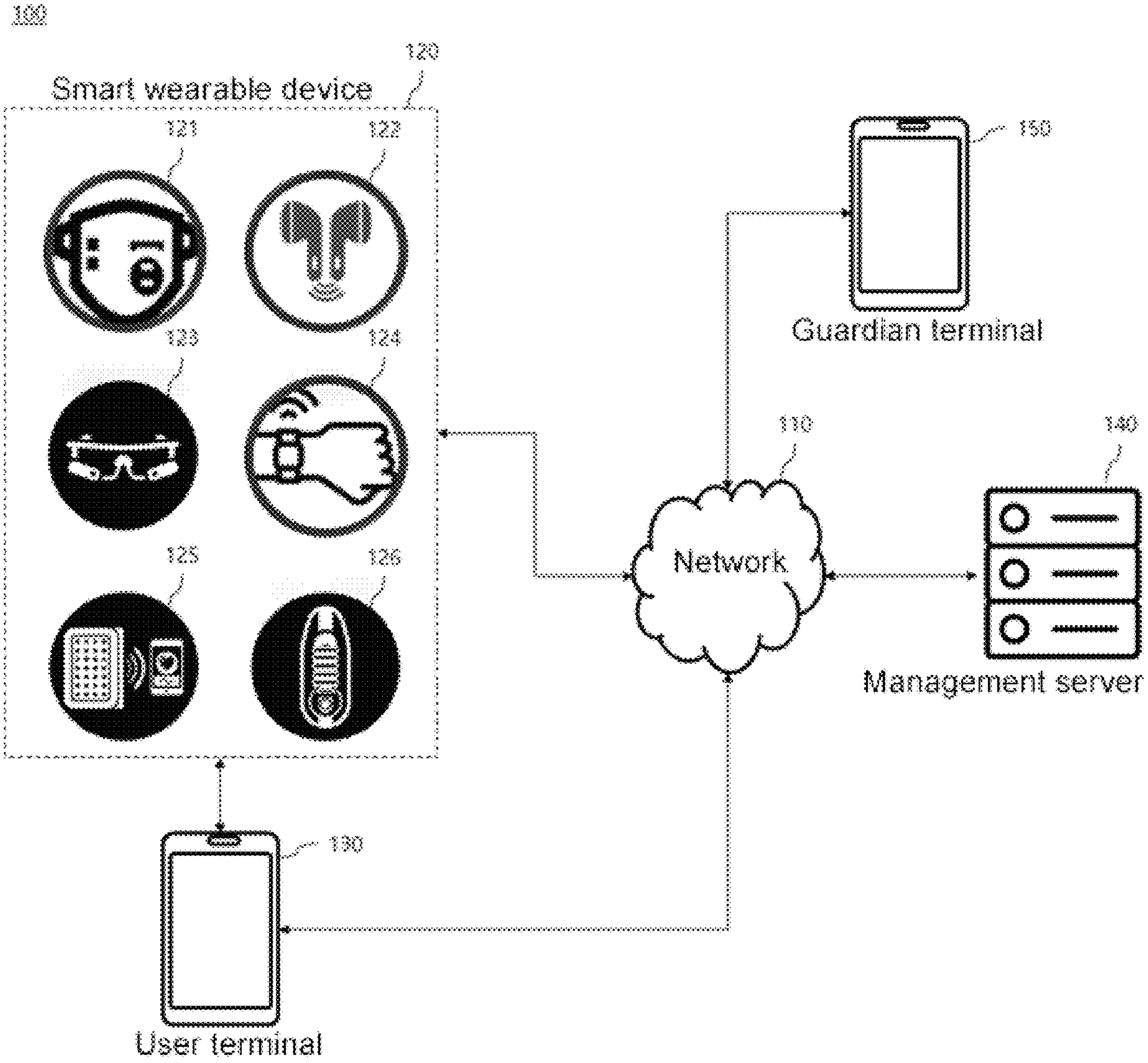
FIG. 1 is a diagram illustrating the structure of a biometric information-based access management system.

Various modifications and changes may be made to the present disclosure and the disclosure may include various example embodiments. Specific example embodiments are described in detail with reference to the accompanying drawings. The example embodiments, however, may be embodied in various forms, and should not be construed as being limited to only the specific example embodiments. Rather, the example embodiments should be understood to include all the modifications, equivalents, and substitutions included in the spirit and technical scope of the disclosure.

When adding reference numerals to the components of each drawing, it should be noted that the same components are given the same reference numerals as much as possible even though they are indicated on different drawings. In addition, in describing the present disclosure, if it is determined that a detailed description of a related known configuration or function may obscure the gist of the present disclosure, the detailed description thereof will be omitted.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Although the terms "first", "second", "A", "B", "(a)", "(b)", etc., may be used herein to describe various components, the components should not be limited by these terms. These terms are only used to distinguish one component from another component. For example, a first component may also be termed a second component and, likewise, a second component may be termed a first component, without departing from the scope of this disclosure.

When a component is referred to as being "connected to" or "coupled to" another component, the component may be directly connected to or coupled to the other component, or one or more other intervening components may be present. In contrast, when a component is referred to as being "directly connected to" or "directly coupled to", there is no intervening component.

As used herein, "comprises" and/or "comprising" refers to a referenced component, step, operation and/or element of one or more other components, steps, operations and/or elements. The presence or addition is not excluded.

A component included in one embodiment and a component having a common function may be described using the same name in another embodiment. Unless otherwise stated, the descriptions in any one embodiment may be applied to other embodiments, and specific descriptions may be omitted within the overlapping range or within the range that can be clearly understood by those skilled in the art.

Hereinafter, example embodiments will be described in detail with reference to the accompanying drawings.

FIG. 1 is a diagram illustrating the structure of the biometric information-based access management system.

In FIG. 1, the biometric information-based access management system 100 is comprised of a network 110, a smart wearable device 120, a user terminal 130, a management server 140, and a guardian terminal 150.

The access management system 100 may refer to a system for managing people to a specific management space. For example, the manager of the access management system 100 may allow or restrict the entry of people to a space where people are concentrated in the same space, such as a restaurant or a school.

The access management system 100 may be implemented in an electronic manner. For example, the processes for implementing the access management system 100 may be provided in the form of a computer program or a mobile application, and the user terminal 130, the management server 140, and the guardian terminal 150 can run computer programs or mobile applications.

In the access management system 100, data and information can be traded through network. For example, network 110 can be a wireless data communication network such as LTE, 5G, 6G, WLAN or Wi-Fi. Meanwhile, the smart wearable device 120 and the user terminal 130 may exchange data through the network 110 or may exchange data through short-range wireless communication such as Bluetooth.

The user terminal 130 may mean a terminal of a user who wants to enter the management space managed by the access management system 100, and the guardian terminal 150 may mean a terminal that receives notice when an emergency, such as the spread of an infectious disease, occurs to the user. For example, the user terminal 130 and the guardian terminal 150 may be mobile devices such as smartphones or tablets, PCs such as desktops or laptops, or other types of electronic devices.

The management server 140 may complete processes necessary for the operation of the access management system 100. For example, the management server 140 may be an application server for providing computer programs or mobile applications that implement the access management system 100.

The smart wearable device 120 may refer to IoT devices that are directly worn on a user's body and measure various types of biometric data. For example, the smart wearable device 120 may include a smart mask 121, with the addition of a wireless headset 122, smart glasses 123, a smart watch 124, a smart healthcare patch 125, and smart sneakers 126.

The access management system 100 may determine whether an authentication condition is satisfied when the user enters the management space and may approve or reject the user's authentication request based thereon. Whether the authentication condition is satisfied or not may be based on the user's biometric data and authentication data, and the access management system 100 may continuously check whether the authentication condition is satisfied even after the user enters. Since whether the authentication condition is satisfied may be determined based on data directly measured from the user's body by the smart wearable device 120, the access management system 100 may be operated more efficiently and accurately.

Figure 2:
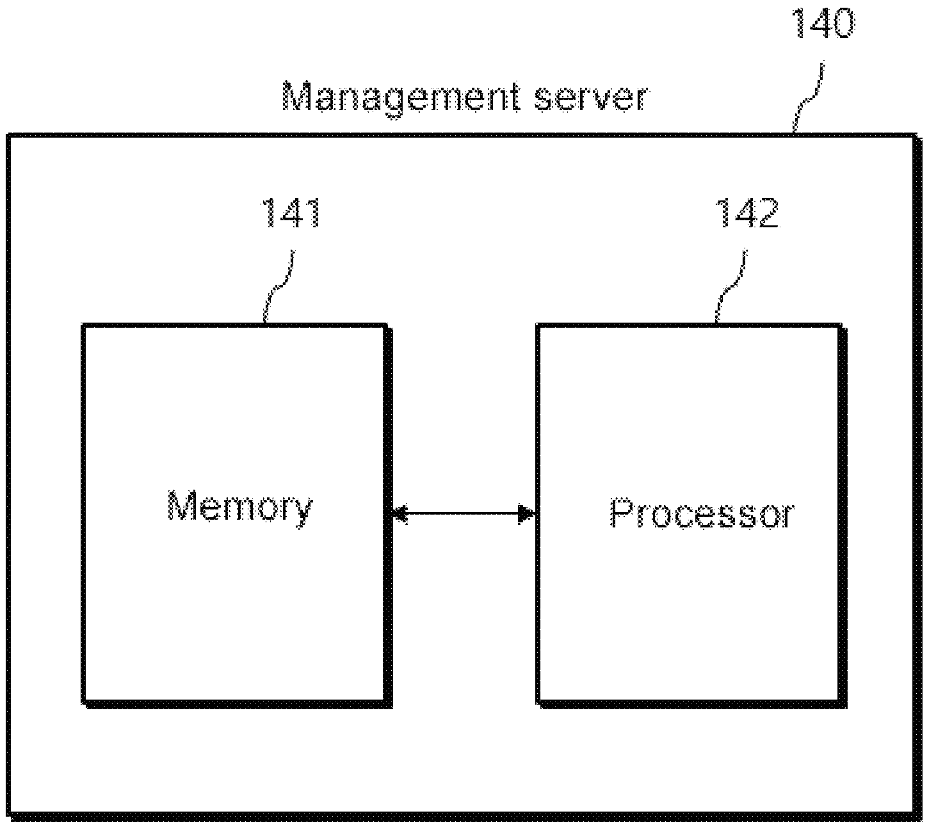
FIG. 2 is a diagram for explaining elements constituting a management server for operating a biometric information-based access management system.

FIG. 2 is a diagram for explaining elements constituting a management server for operating an access management system based on biometric data.

In reference to FIG. 2, the management server 140 for operating the biometric information-based access management system 100 may include a memory 141 and a processor 142. However, the present invention is not limited thereto, and other general-purpose elements such as a communication module may be further included in the management server 140.

The management server 140 may be an electronic device configured to operate the access management system 100. For example, the management server 140 may be a server device for hosting computer programs or mobile applications that implement the access management system 100 or other type of computing device.

The memory 141 may have a structure for storing various commands or data processed by the management server 140. For example, the memory 141 may be a non-volatile memory such as ROM, PROM, EPROM, EEPROM, flash memory, PRAM, MRAM, RRAM, FRAM, or a volatile memory such as DRAM, SRAM, SDRAM, PRAM, RRAM, FeRAM, etc., and may be implemented in the form of HDD, SSD, SD, Micro-SD, or the like, or a combination thereof.

The processor 142 may have a structure for completing processes required for the operation of the access management system 100. The processor 142 may be implemented as an array of a plurality of logic gates or a general-purpose microprocessor for processing various operations inside the management server 140 and may be configured as a single processor or a plurality of processors. For example, the processor 142 may be implemented in the form of at least one of a CPU, a GPU, and an AP.

The processor 142 executes the commands saved in the memory 141, thereby receiving authentication requests regarding the management space of the access management system 100 and the user's biometric data collected by the smart mask 121 from the user terminal 130.

The smart mask 121 may measure biometric data including body temperature, humidity, and whether the mask is worn, and send it to the user terminal 130. The user terminal 130 may send an authentication request for biometric data and management space to the management server 140.

The processor 142 executes the commands saved in the memory 141 to determine whether the user satisfies the authentication condition of the management space based on the biometric data and the authentication data of the user retrieved from the public database.

For example, authentication data such as the user's disease infection history, vaccination information, and overseas travel history may be inquired from the public database, and whether the authentication conditions are satisfied may be determined based on the biometric data and authentication data. For example, the authentication condition for allowing the user to enter may be a combination of a normal condition, a mask-wearing condition, a vaccination condition, and other conditions.

The processor 142 may be configured to send to the user terminal 130 an approval message for the authentication request and periodic data requests when the authentication condition is satisfied by executing commands saved in the memory 141.

When the approval message is sent to the user terminal 130, the user can enter the management space by showing the approval message to the manager of the access management system 100, for example, the person in charge of access to the management space, through the app screen or the like. Meanwhile, periodic data requests may be sent to the user terminal 130 to continuously monitor whether the user's health status is changed or deteriorated after admission.

The processor 142 periodically receives from the user terminal 130 the position of the smart mask 121 and subsequent biometric data of the user generated in response to periodic data requests by executing commands saved in the memory 141.

When periodic data requests are sent to the user terminal 130, the user terminal 130 may periodically receive subsequent biometric data and location information from the smart mask 121. For example, data such as the user's body temperature, humidity, and whether the mask is worn, measured every 30 minutes, may be sent to the user terminal 130 as subsequent biometric data, and the GPS location of the smart mask 121 may be sent. The location of the smart mask 121 may be utilized to determine whether the user continues to stay in the management space or has left the management space.

By executing the commands saved in the memory 141, the processor 142 may be configured to send an authentication failure message to the user terminal 130 based on the subsequent biometric data and the user's subsequent authentication data periodically received, while the smart mask 121 is in the management space.

Subsequent biometric data periodically measured by the smart mask 121 may be continuously provided to the management server 140, and subsequent authentication data may also be periodically queried from a public database. Therefore, even when the user's health condition deteriorates, or the inquiry history of the authentication data updates, such a change can be recognized by the management server 140, and accordingly, whether the authentication condition is satisfied can be changed. If the authentication condition is not satisfied while the smart mask is in the management space, an authentication failure message can be sent to the user terminal 130, and the user can check their health status or whether the mask is worn appropriately.

On the other hand, the biometric data and subsequent biometric data may include the user's body temperature measured by the smart mask 121, the internal humidity of the mask, and whether the mask is worn appropriately, while the authentication data and subsequent authentication data may include the user's disease infection history, vaccination information, and overseas travel history.

Figure 3:
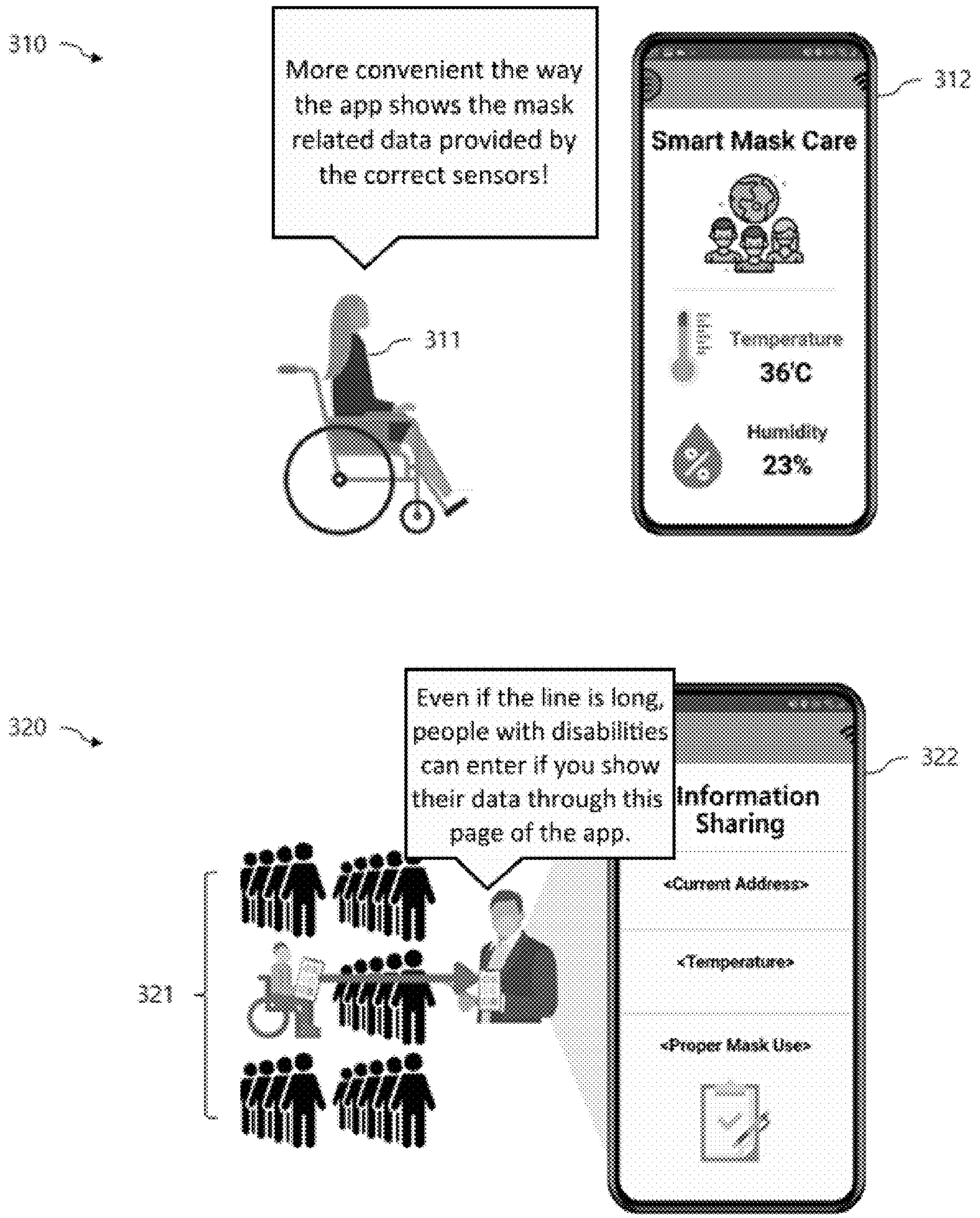
FIG. 3 and FIG. 4 are diagrams for explaining examples in which a biometric information-based access management system is utilized.
Figure 4:
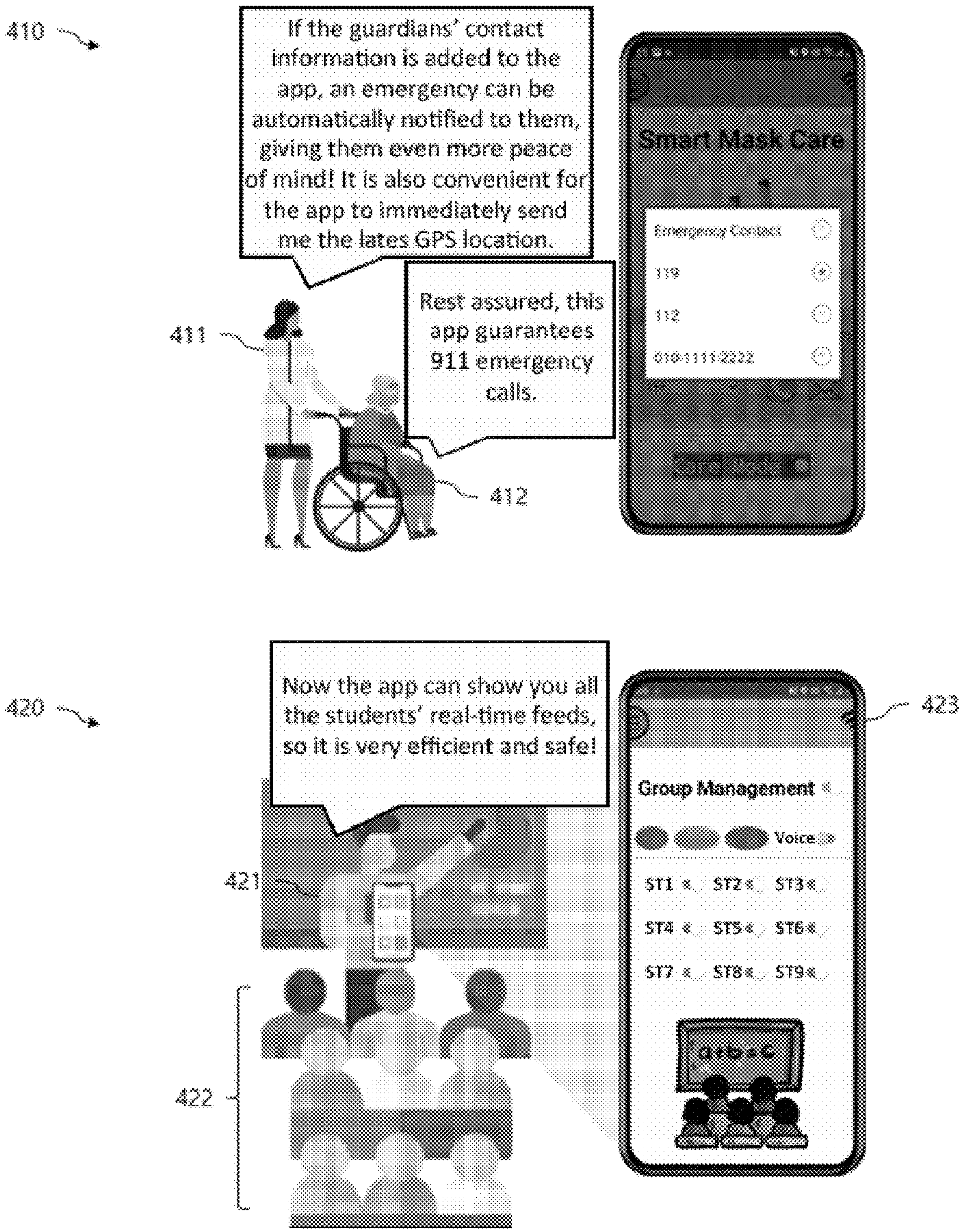

FIG. 3 and FIG. 4 are diagrams for explaining examples in which a biometric information-based access management system is utilized.

In reference to FIG. 3, examples 310 and 320 in which the biometric information-based access management system 100 is utilized may be illustrated.

As in the example 310, even when the user 311 is a patient with poor mobility, biometric data measured through the smart wearable device 120 including the smart mask 121 may be displayed on the user terminal 312. Therefore, the biometric data of the user 311 can be conveniently and accurately provided without the inconvenience of the access manager of the management space directly measuring the body temperature of the user 311.

Particularly, in the example 320, even when the waiting line for users 321 to enter the management space is long, if the users 321 show their respective user terminals 322 to the access manager, manual access management can be performed with higher efficiency compared to the method of measuring body temperature and checking QR code.

In reference to FIG. 4, examples 410 and 420 in which the biometric information-based access management system 100 is utilized may be illustrated.

As in the example 410, the access management system 100 may additionally provide a health abnormality notification function. For example, when the guardian 411 of the patient 412 registers his/her contact information in the access management system 100, if the biometric data of the patient 412 is out of the normal range, the guardian terminal 150 of the guardian 411 can be notified. The health abnormality notification function may be provided together with an access management function.

Regarding the health abnormality notification function, the processor 142 determines whether a health abnormality event has occurred to the user 412 based on the biometric data and subsequent biometric data, and when the health abnormality event occurs, the access management system 100 may be configured to send a health abnormality notification message to the guardian terminal 150 of the user's guardian 411.

In the same manner as above, even when a sudden deterioration of health occurs to the user 412 after the user 412 enters the management place, the user's guardian 411 receives a health abnormality notification message through the guardian terminal 150. For example, the health abnormality event may mean a sudden rise in body temperature of the user 412 or a difficulty with breathing.

Meanwhile, when sending the health abnormality notification message, the processor 142 classifies a level of urgency of the health abnormality event into any one of high, medium, and low based on a degree and a number of times that the biometric data and the subsequent biometric data deviate from a health threshold range, and it sends an authentication failure message in case of low level of urgency, provides an additional emergency call to the guardian terminal in case of medium level of urgency, and delivers an additional emergency contact to the emergency protection center in case of high level of urgency.

For example, as the health threshold range, the normal body temperature threshold may be set to 37° C., and the high, medium, and low level of urgency can be determined according to the number of times and the number in which the body temperature exceeds 37° C. in the biometric data and subsequent biometric data. As the level of urgency increases, additional notifications can be sent, so that appropriate actions can be taken according to the level of urgency.

As in the example 420, a group management function for a plurality of users such as students may be provided through the access management system 100. For example, the teacher 421 may serve as a manager of the access management system 100, and the teacher terminal 423 of the teacher 421 may serve as the management server 140, and the students 422. authentication states may be provided to the teacher terminal 423.

With respect to the group management function, the user may be one of the plurality of users 422 forming the group, and the processor 142 determines whether each of the plurality of users 422 meets the authentication condition of the management space. It may be further configured to provide the indicating group authentication status to an administrator of the management server. In this way, authentication states of a plurality of users 422 such as students or patients may be collectively managed.

Figure 5:
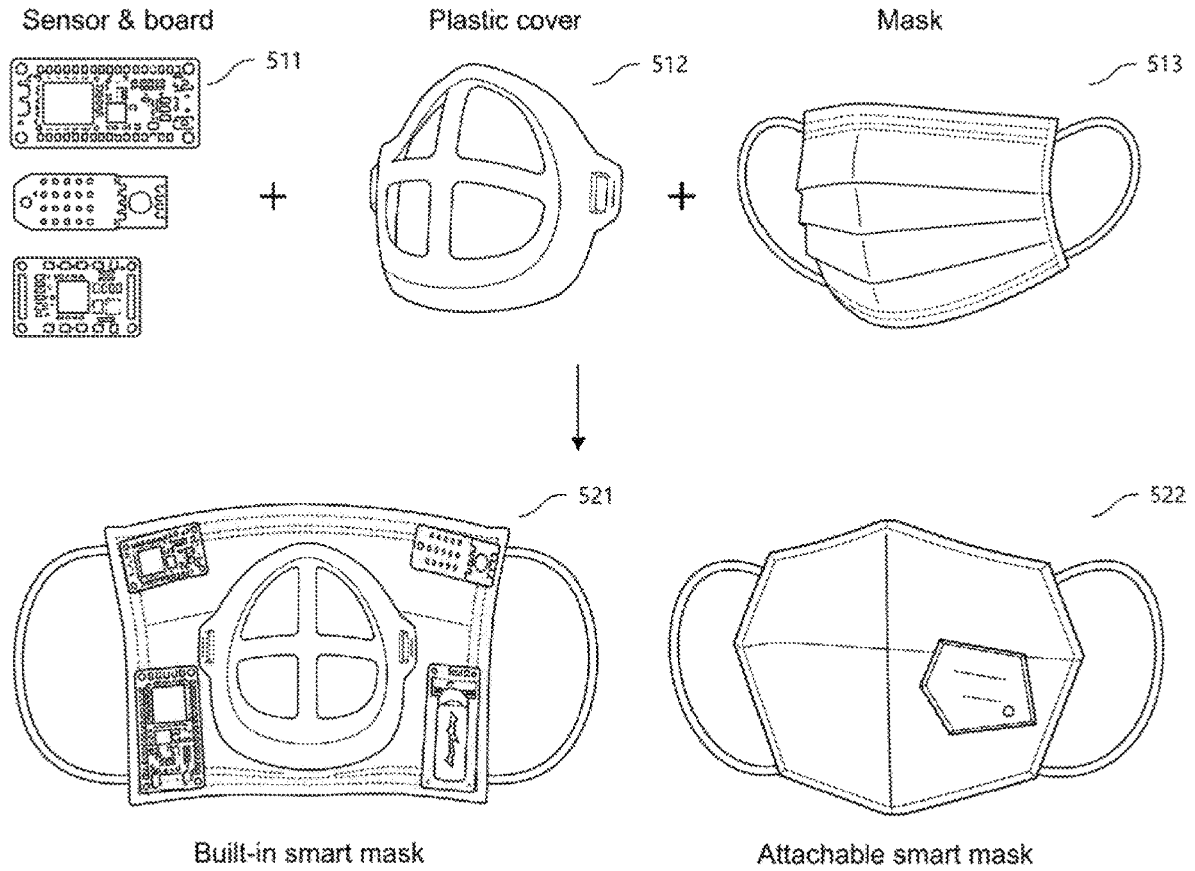
FIG. 5 is a diagram for explaining implementation examples of a smart mask utilized in a biometric information-based access management system.

FIG. 5 is a diagram for explaining implementation examples of a smart mask utilized in a biometric information-based access management system.

In reference to FIG. 5, examples 521 and 522 of the smart mask 121 used in the biometric information-based access management system 100 may be illustrated.

For example, the smart mask 121 may include a sensor & board 511, a plastic cover 512, and a mask 513. The sensor & board 511 may include a temperature sensor for body temperature measurement, a humidity sensor for respiration measurement, an infrared sensor for measuring whether a mask is worn, and a data-processing board. The board for data processing may be an ESP8266 board. The plastic cover 512 may form a frame of the entire mask, or the sensor & board 511 may be embedded therein.

By a combination of the sensor & board 511, the plastic cover 512 and the mask 513, the smart mask 121 may be implemented as in the implementation examples 521 and 522, and the implementation example 521 may be a built-in smart mask, while the implementation example 522 may be an attachable smart mask.

Figure 6:
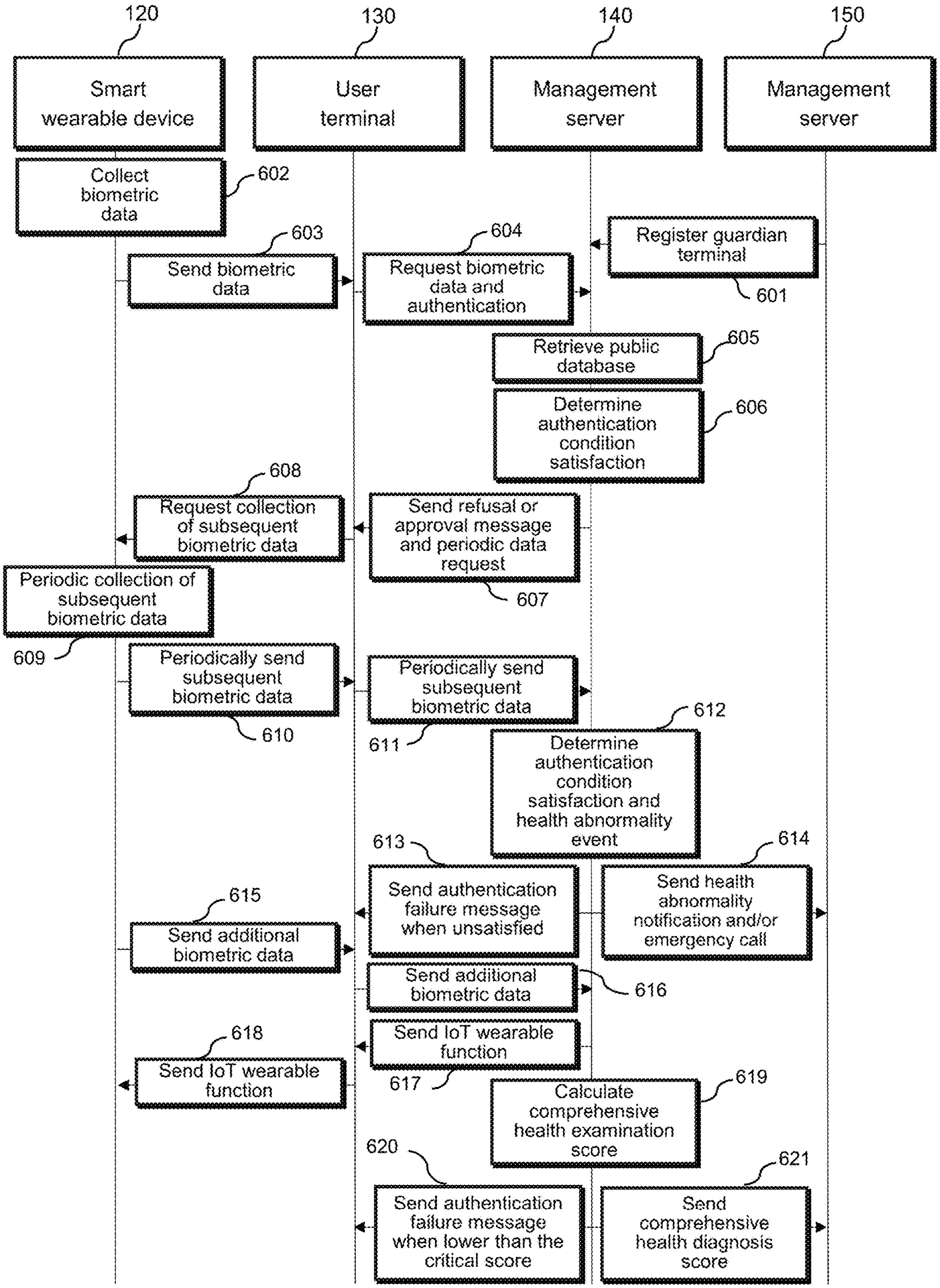
FIG. 6 is a diagram for explaining the operation of the biometric information-based access management system.

FIG. 6 is a diagram for explaining the operation of the biometric information-based access management system.

In reference to FIG. 6, a process 600 in which the biometric information-based access control system 100 operates is performed by the smart wearable device 120, the user terminal 130, the management server 140, and the steps from 601 to 621 which are executed in the guardian terminal 150.

Steps 602 to 613 may correspond to the executive processes of the management server 140 described above with reference to FIG. 2 and may correspond to steps of the management method 1200 to be described later with reference to FIG. 12.

On the other hand, when the guardian terminal 150 is registered in advance in the access management system 100 as in step 601, health abnormality notification can be sent to the guardian terminal 150 or an emergency call can be provided as in step 614 as described above in FIG. 4.

Steps 615 to 621 may refer to a process of providing at least one IoT wearable function to a user through at least one additional wearable device. In relation to steps 615 to 621, the processor 142 receives, from the user terminal 130, additional biometric data measured through at least one additional wearable device worn by the user and may be further configured to provide at least one IoT wearable function to the user through the user terminal 130 based on the additional biometric data.

For example, at least one additional wearable device may include at least one of wireless headset 122, smart glasses 123, a smart watch 124, a smart healthcare patch 125, and smart sneakers 126, with the addition of biometric data, meaning the data measured from the user's body through the devices, from steps 615 and 616.

At least one IoT wearable function is activated based on additional biometric data measured from at least one of the wireless headset 122, smart glasses 123, smart watch 124, smart healthcare patch 125, and smart sneakers 126 may be executed, which in turn may be communicated to the user terminal 130 and the smart wearable device 120 as in steps 617 and 618.

At least one IoT wearable function includes a body temperature correction function through the wireless headset 122, a user vision information provision function through the smart glasses 123, a detailed health data provision function through the smart watch 124, a local area diagnosis function through the smart healthcare patch 125, and a motion abnormality detection function through the smart sneakers 126. For details of at least one IoT wearable function, reference may be made to FIGS. 7 to 11, which will be described later.

Meanwhile, as in steps 619 to 621, the user's comprehensive health diagnosis score may be calculated based on at least one IoT wearable function. In this case, the comprehensive health examination score may supplement the access management function of the access management system 100 to determine, in more detail, whether the user satisfies the authentication condition. For example, if the user's comprehensive health examination score is calculated in step 619, an authentication failure message may be sent to the user terminal 130 as in step 620 based on the calculation, and a comprehensive health diagnosis may be provided to the guardian terminal 150, as in step 621.

That is, the processor 142 calculates a comprehensive health examination score of the user based on at least one of the body temperature correction function through the wireless headset 122, the user vision information provision function through the smart glasses 123, the detailed health data provision function through the smart watch 124, the local area diagnosis function through the smart healthcare patch 125, and the motion abnormality detection function through the smart sneakers 126, and determine whether the user satisfies the authentication condition by additionally considering whether the comprehensive health examination score exceeds a threshold score set according to the age, gender, and occupation of the user.

Specifically, the user's comprehensive health diagnosis score can be calculated based on the body temperature corrected through the wireless headset 122, the user vision information provided through the smart glasses 123, detailed health data such as blood pressure, blood sugar, pulse rate, and blood flow provided through the smart watch 124, diagnosis state of a local area such as a surgical site provided through the smart healthcare patch 125, and the user's exercise information or behavioral abnormality provided through the smart sneakers 126.

When the comprehensive health examination score is lower than the critical score, this may mean that the current user's immunity and physical strength are low, and thus the user may be vulnerable to infectious diseases. Accordingly, to prevent the concentration of a large group of people in the management space, re-examination can be initiated to see whether the authentication condition is met, and an authentication failure message may be sent to the user terminal 130. Meanwhile, the threshold score may be statistically set to a different value for each user in consideration of characteristics such as age, gender, and occupation. In this way, when the comprehensive health examination score is used, the probability that the user is infected with an infectious disease in the management space can be greatly reduced.

FIG. 7 to FIG. 11 are diagrams for explaining a method of providing at least one IoT wearable function by utilizing at least one additional wearable device.

Figure 7:
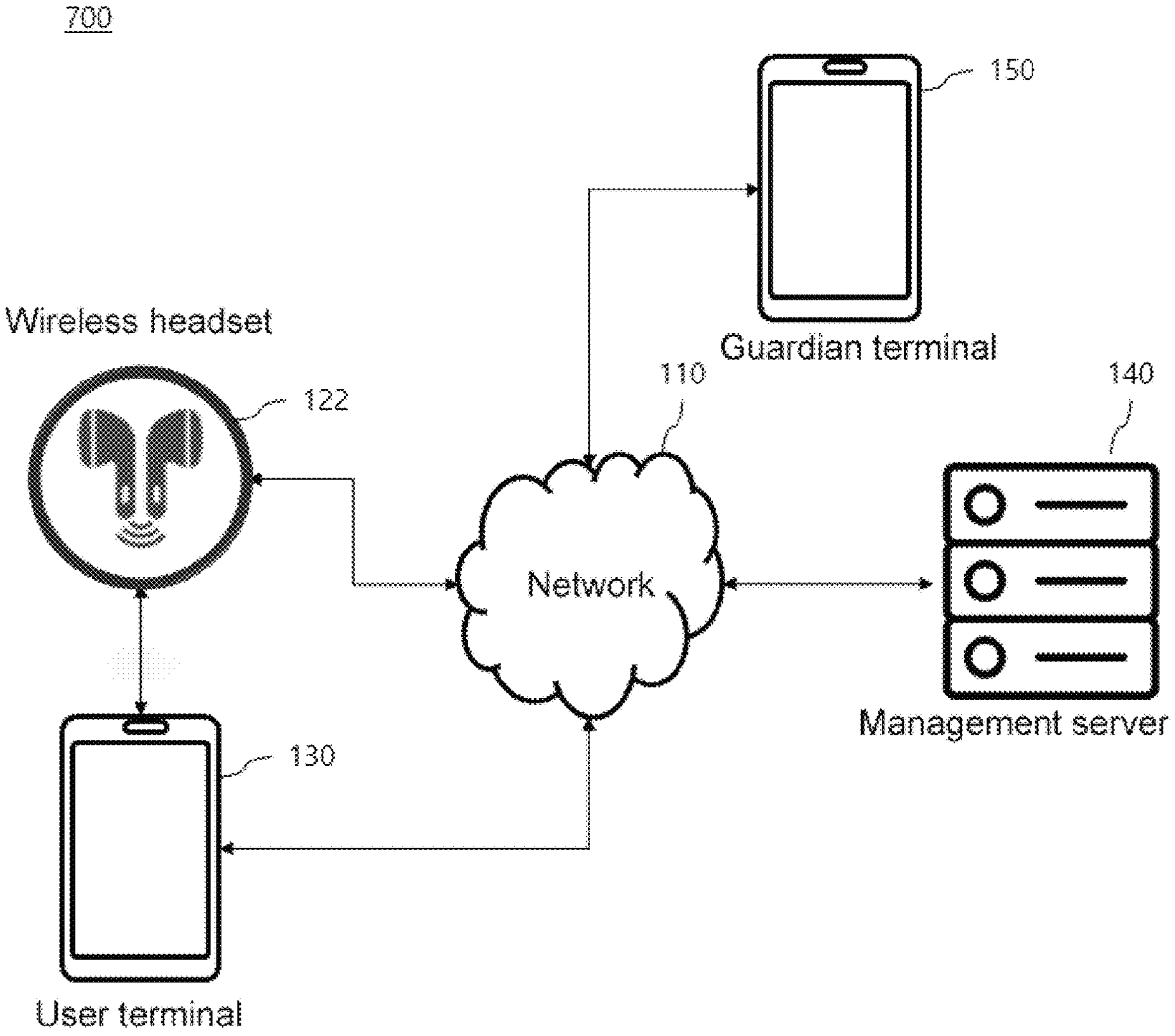
FIG. 7 to FIG. 11 are diagrams for explaining a method of providing at least one IoT wearable function by utilizing at least one additional wearable device.

In reference to FIG. 7, a body temperature correction function through the wireless headset 122 may be explained. The wireless headset 122 may include an additional temperature sensor formed in a part that's in direct contact with the user's ear, and the user's body temperature measured by the smart mask 121 can be corrected through the additional body temperature data measured through the wireless headset 122.

Figure 8:
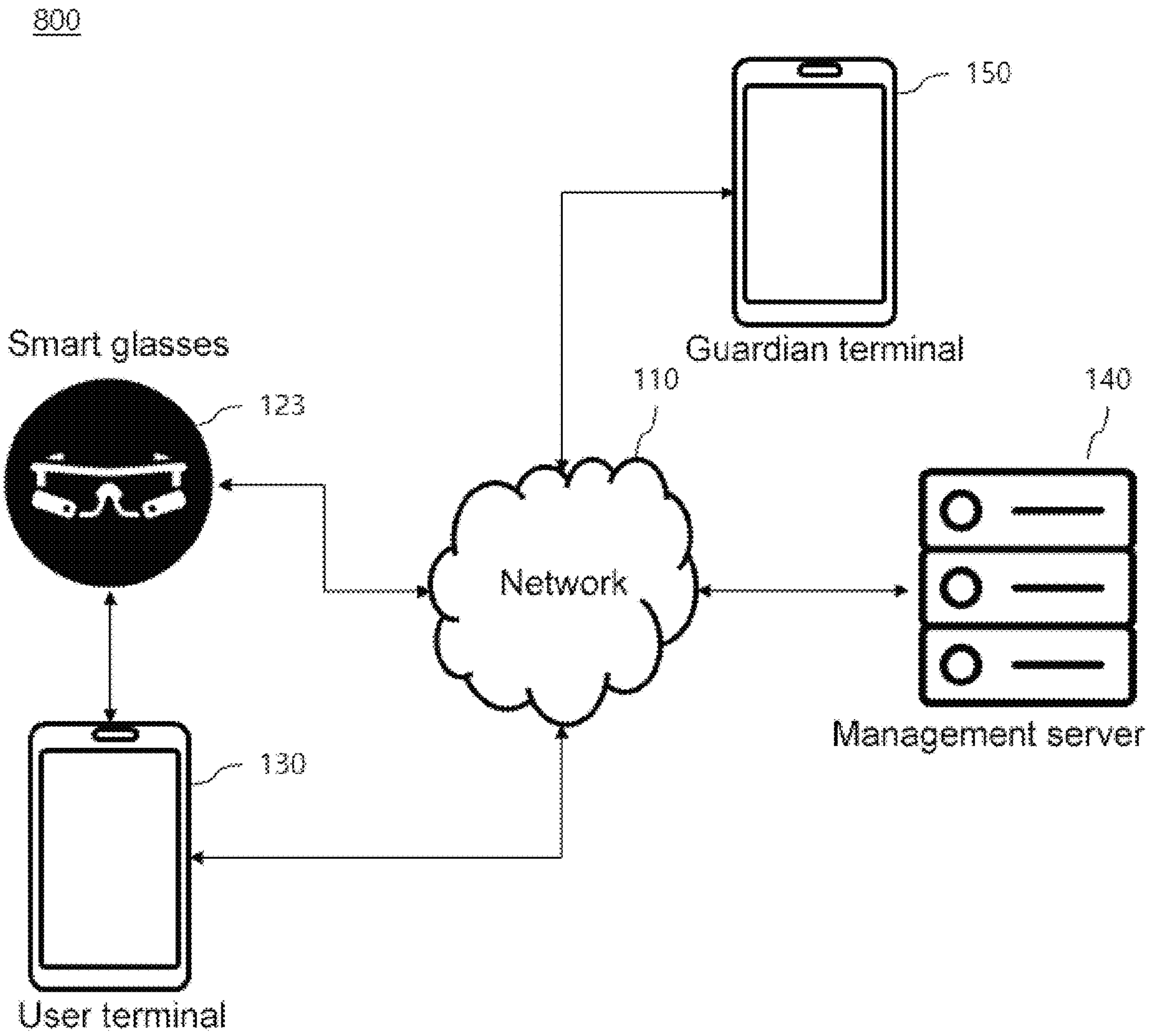

In reference to FIG. 8, a function of providing user vision information through the smart glasses 123 may be described. The smart glasses 123 may be directly worn around the user's eyes to provide a variety of visual information to the user, and the user's current first-person vision information may be recorded. Therefore, when the user's vision information is provided to the management server 140 through the smart glasses 123, health information such as what the user is seeing, whether the user is lying on the floor, etc. can be derived.

Figure 9:
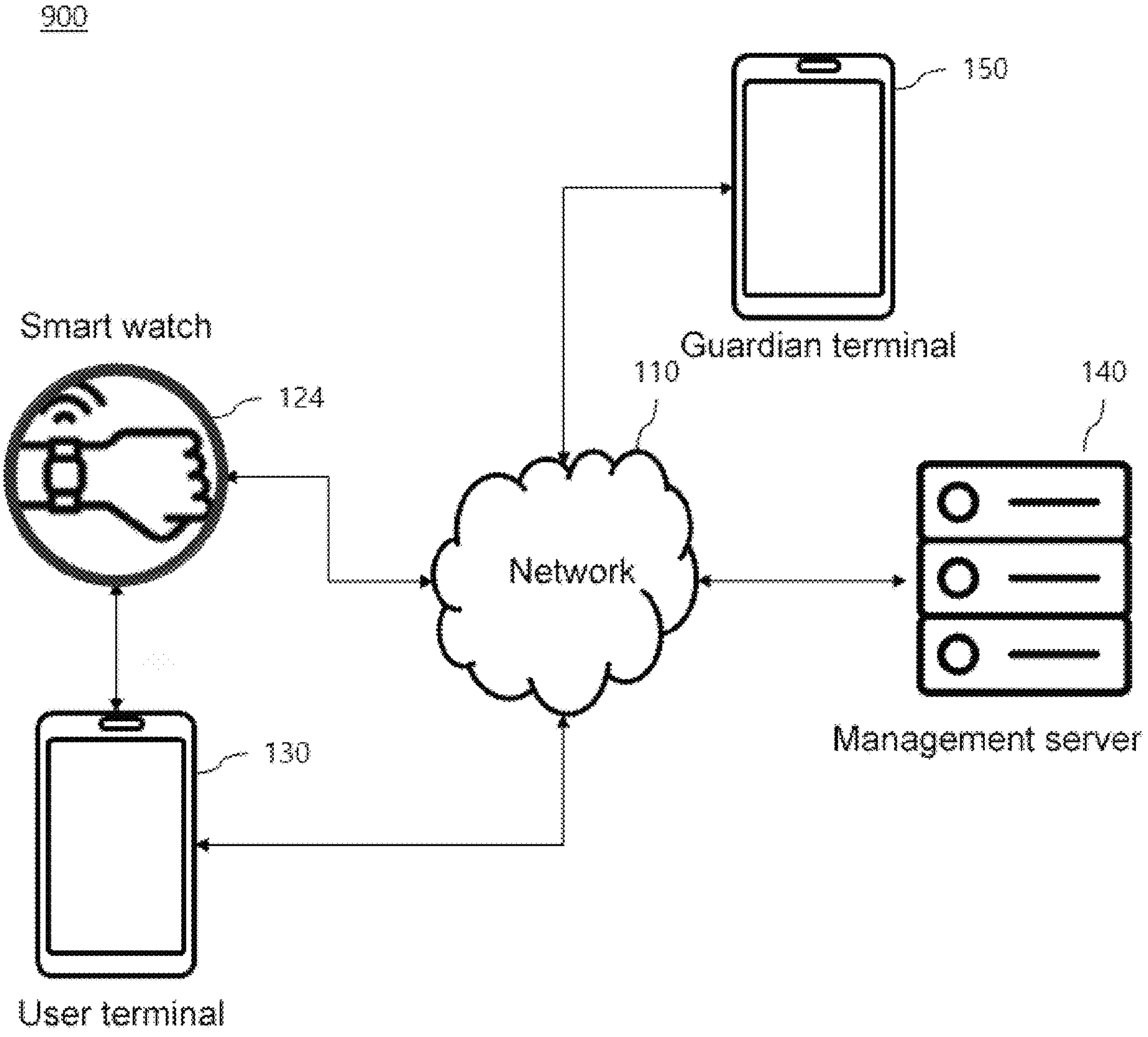

In reference to FIG. 9, a function for providing detailed health data through the smart watch 124 may be described. The smart watch 124 may be directly worn on a user's wrist to measure detailed health data such as blood pressure, blood sugar, blood flow, and pulse rate of the user. Particularly, when the user has an underlying disease such as high blood pressure or diabetes, the user's current health state can be checked through monitoring of detailed health data, and from it, whether the user is currently vulnerable to an infectious disease can be derived.

Figure 10:
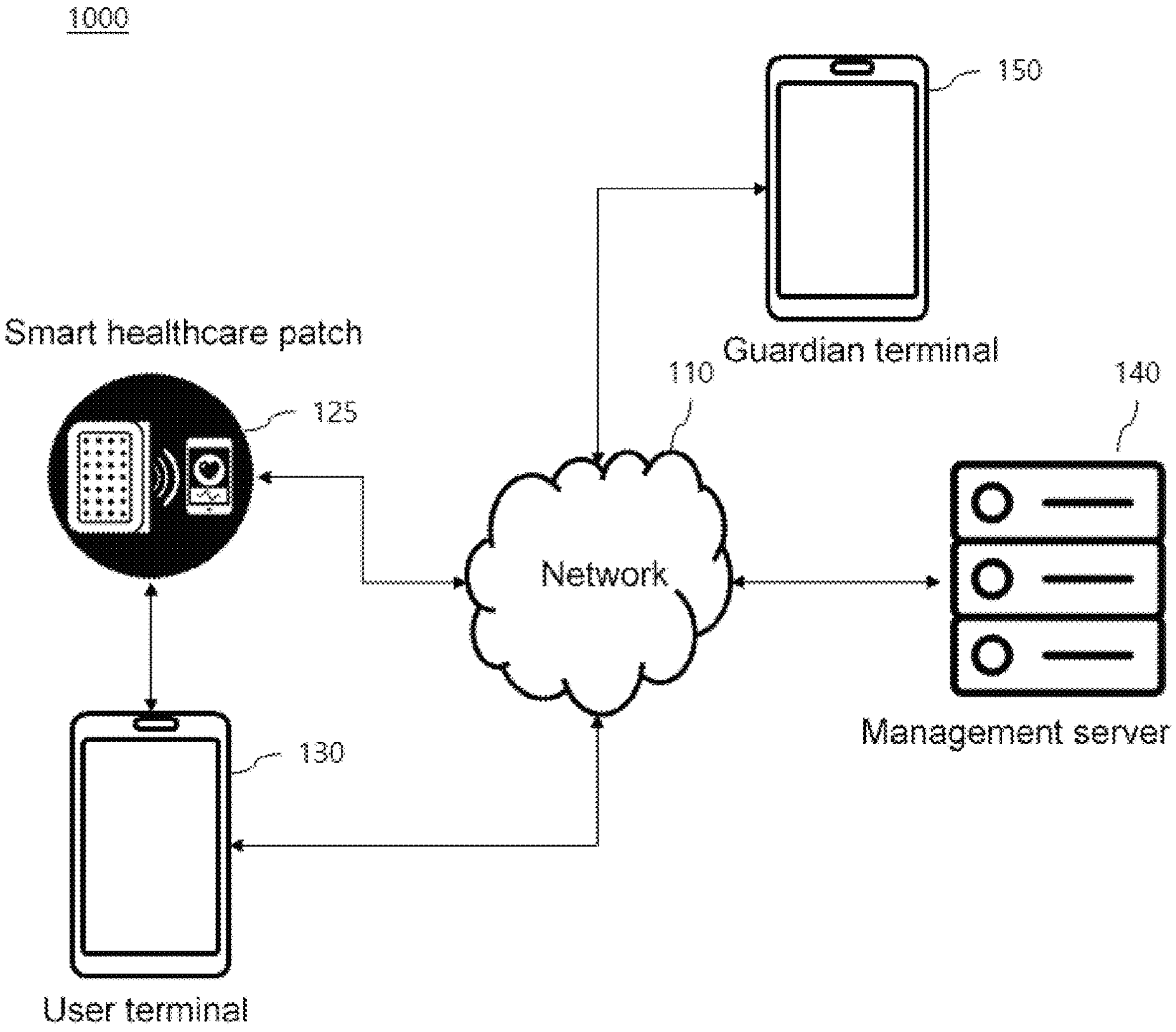

In reference to FIG. 10, a local area diagnosis function through the mart healthcare patch 125 may be described. The smart healthcare patch 125 may be directly attached to a local area of the user's body, such as a surgical site or a painful area, to measure local body temperature, inflammation, and other status information of the local area. Particularly, if the user is a patient who has recently undergone surgery, whether the user's current health status and infectious disease should be considered through the smart healthcare patch 125 may be derived.

Figure 11:
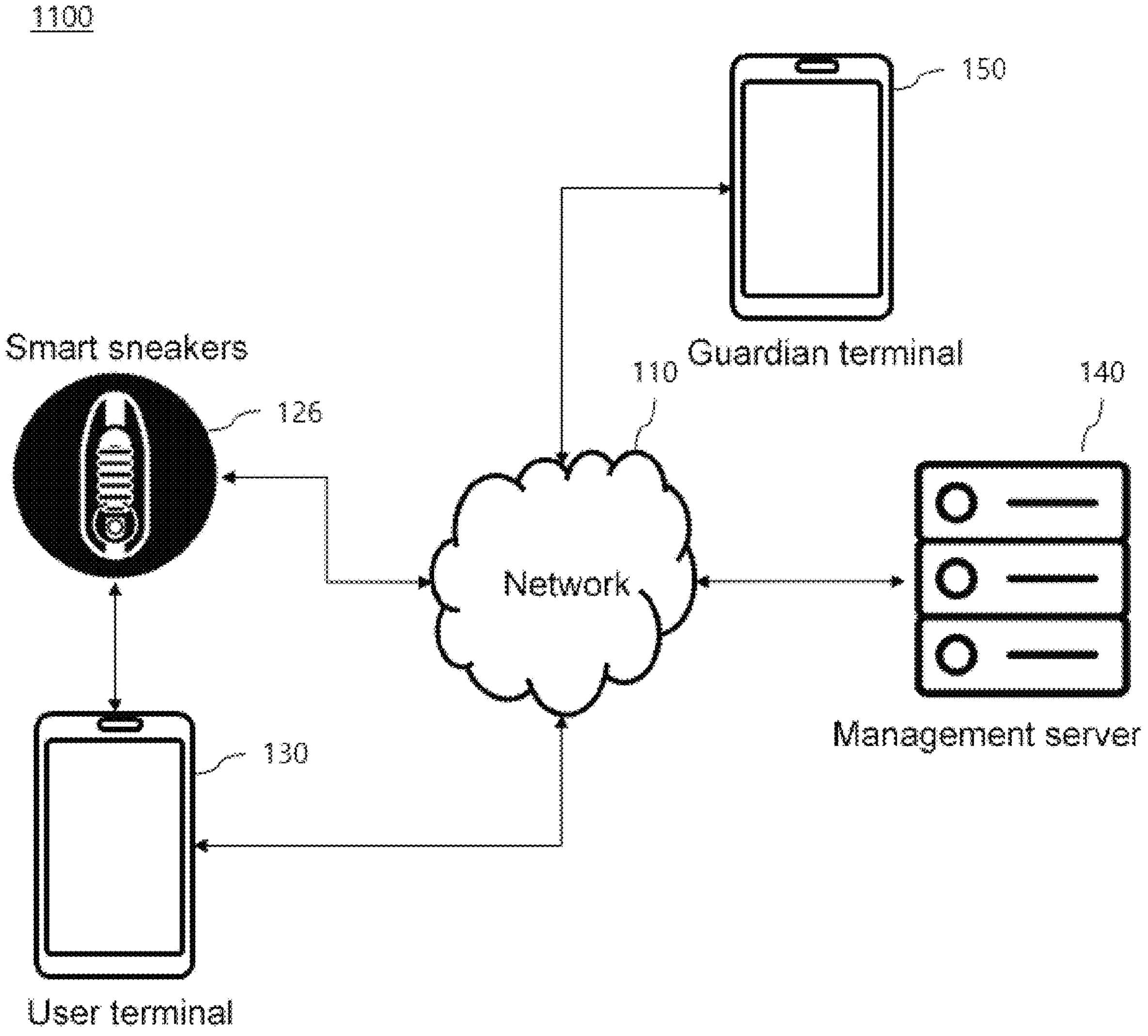

In reference to FIG. 11, a behavior abnormality detection function through the smart sneakers 126 may be described. The smart sneakers 126 may be directly worn on the user's foot to measure data related to the user's movement. For example, the smart sneakers 126 may include a gyroscope for measuring the acceleration according to the user's movement, and through this, the user's abnormal behavior such as the user's moving distance being equal to the amount of exercise or whether the user has fallen, can be derived.

Figure 12:
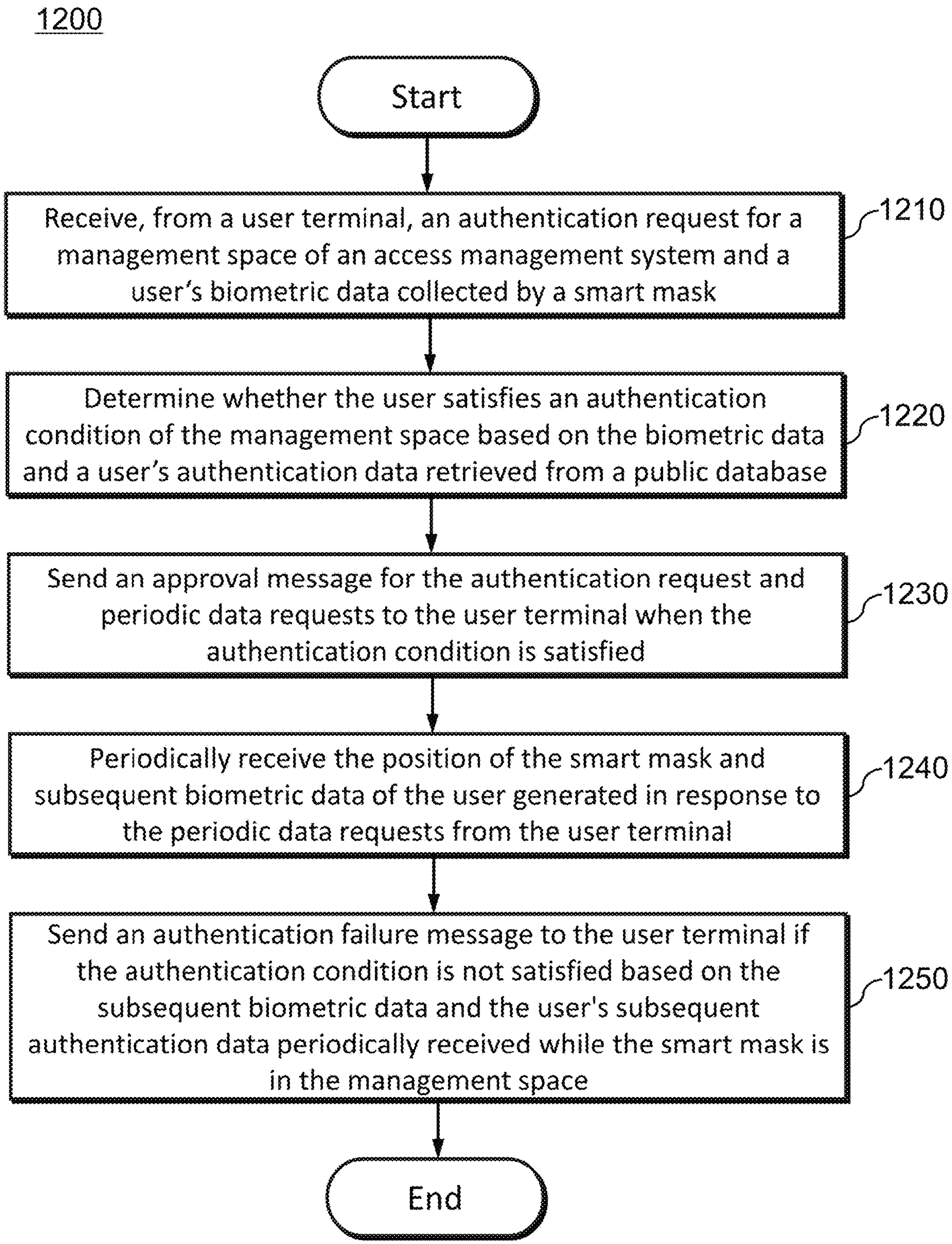
FIG. 12 is a diagram for explaining steps of configuring a management method for operating a biometric information-based access management system.

FIG. 12 is a diagram for explaining steps of configuring a management method for operating an access management system based on biometric data.

In reference to FIG. 12, a management method 1200 for operating the biometric information-based access management system 100 may include steps 1210 to 1250. However, the present invention is not limited thereto, and other general-purpose steps not shown may be further included in the management method 1200.

The management method 1200 may include steps that are time-series processed by the management server 140. Therefore, even if omitted below, the contents described above for the management server 140 may be equally applied to the management method 1200.

The management method 1200 may be performed by the processor 142 executing instructions stored in the memory 141.

In step 1210, the management server 140 may receive, from the user terminal 130, an authentication request for the management space of the access management system 100 and the user's biometric data collected by the smart mask 121.

In step 1220, the management server 140 may determine whether the user satisfies the authentication condition of the management space based on the biometric data and the user's authentication data retrieved from the public database.

In step 1230, the management server 140 may send an approval message for the authentication request and periodic data requests to the user terminal 130 when the authentication condition is satisfied.

In step 1240, the management server 140 may periodically receive from the user terminal 130 the location of the smart mask 121 and subsequent biometric data of the user-generated response to periodic data requests.

In step 1250, the management server 140 determines that, while the location of the smart mask 121 is in the management space, an authentication failure message may be sent to the user terminal if the authentication condition is not satisfied based on the subsequent biometric data and the user's subsequent authentication data periodically received.

Meanwhile, the management method 1200 for operating the biometric information-based access management system 100 may be implemented in the form of a computer program stored in a computer-readable storage medium. That is, the computer program may include commands for implementing the management method 1200, and the commands of the computer program may be saved in a computer-readable storage medium.

In accordance with the present invention, since approval of the authentication request may be determined based on the user's authentication data retrieved from the public database and biometric data directly measured from the user's body by a wearable device such as a smart mask, compared to the existing method of manually checking QR code and body temperature, biometric data such as body temperature can be measured more accurately, and the hassle of users directly tagging their QR code with the QR code scanner can be reduced, and the accuracy and efficiency of access management can be improved.

Figure 13:
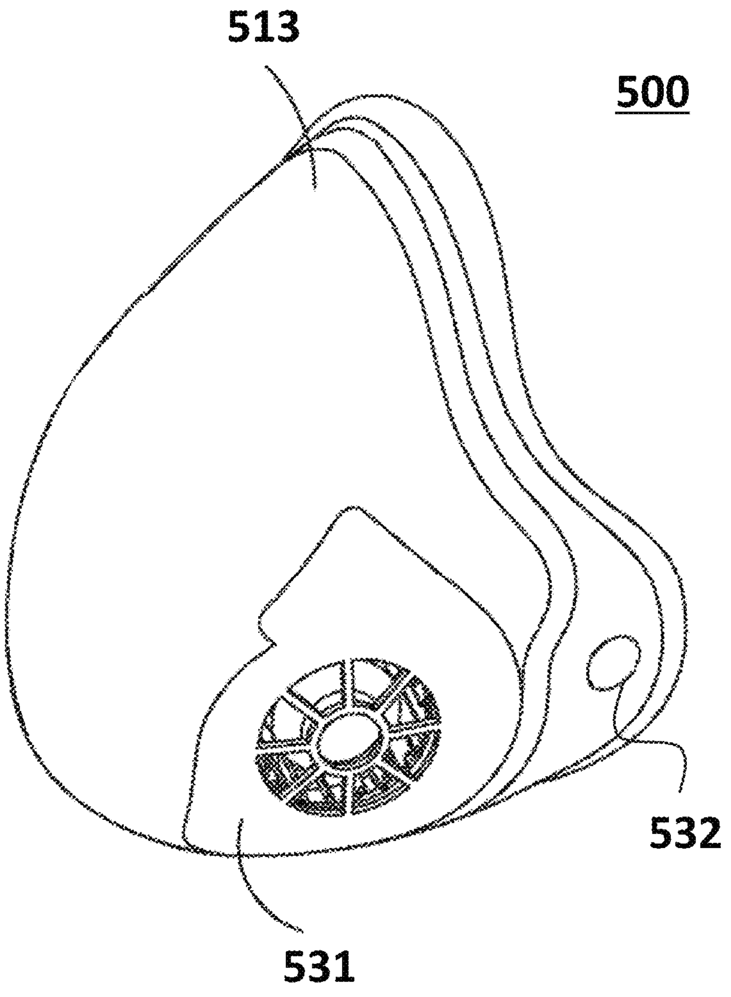
FIG. 13 is a smart mask utilized in a biometric information-based access management system with fan system and indicator system.

FIG. 13 is a smart mask utilized in a biometric information-based access management system with fan system and indicator system.

FIG. 13 illustrates an implementation example of a smart mask 500 utilized in a biometric information-based access management system. The smart mask 500 is designed to monitor and process biometric data of a user while also facilitating controlled air circulation through an integrated fan system. The structure of the smart mask 500 includes multiple functional components, such as a mask body 513, a fan system 531, and an external indicator 532, which work together to enhance user health monitoring and environmental adaptability. The sensor & board system embedded within the smart mask includes a temperature sensor for measuring the user's body temperature, a humidity sensor for detecting respiration levels and mask-wearing status, an infrared sensor to determine whether the mask is properly worn, and a data-processing board for processing sensor data and communicating with the management server.

The mask body 513 forms the main protective structure of the smart mask 500 and is designed to cover the user's nose and mouth while ensuring comfort and proper sealing. The mask body 513 may be composed of multi-layered filtration materials to provide protection against airborne contaminants. Embedded within the mask body 513 are biometric sensors, including a temperature sensor for body temperature measurement and a humidity sensor for detecting respiration patterns. These sensors continuously collect real-time biometric data and transmit it to the access management system for authentication and health assessment purposes.

The fan system 531 is an integral component of the smart mask 500 that regulates air circulation within the mask. This system is configured to adjust the airflow rate dynamically based on biometric data such as the user's breathing rate, body temperature, and the internal humidity levels of the mask. Additionally, the fan system 531 can respond to external environmental data received from the access management system, ensuring optimal ventilation for the user. By controlling airflow, the smart mask 500 helps maintain user comfort while also reducing the risk of overheating or excessive moisture buildup.

The fan system 531 is a key component of the smart mask 500 that regulates airflow based on real-time biometric and environmental data. The fan system 531 comprises an airflow control module, an environmental adaptation module, and a feedback & correction module. The airflow control module adjusts the airflow rate dynamically in response to breathing rate, internal humidity, and external air quality data. The environmental adaptation module interfaces with external databases to receive air pollution levels and temperature variations, modifying the airflow accordingly. The feedback & correction module works in conjunction with a wireless headset to perform body temperature correction, compensating for discrepancies in temperature readings caused by environmental conditions.

The fan system 531 operates in multiple modes, including a normal mode, an increased airflow mode, and a reduced airflow mode. In the normal mode, the fan system 531 maintains a balanced airflow for general use. In the increased airflow mode, the fan system 531 enhances air circulation in response to high breathing rates or elevated body temperature to prevent discomfort. In the reduced airflow mode, the fan system 531 lowers airflow when external conditions are stable or internal humidity is within an acceptable range, conserving battery power.

The external indicator 532 is positioned on the smart mask 500 to provide real-time visual feedback regarding the operational status of the fan system 531. The external indicator 532 can display different colors corresponding to various airflow modes, such as normal, increased, or reduced airflow. This functionality allows the user and external observers to quickly assess the mask's operational state. Additionally, the external indicator 532 may be used as a communication tool within the access management system to indicate whether the mask is properly worn and whether the user meets the required authentication conditions.

In combination with other wearable devices, such as a wireless headset with an additional temperature sensor, the smart mask 500 contributes to a comprehensive health monitoring system. The biometric data collected by the smart mask 500 is transmitted to the access management system, where it is analyzed alongside authentication data retrieved from a public database. If the system detects deviations from predefined health thresholds, an alert may be sent to the user, a guardian terminal, or emergency services based on the urgency level.

The smart mask 500 can be implemented in various configurations, including a built-in smart mask or an attachable smart mask, as described in previous figures. In either configuration, the smart mask 500 integrates a sensor & board system that includes a data-processing board, infrared sensors for mask-wearing detection, and connectivity modules for wireless communication. These components enable the smart mask 500 to function seamlessly within the biometric information-based access management system, ensuring secure and health-conscious access control.

To ensure accurate health monitoring, the smart mask 500 operates in conjunction with additional smart wearable devices, including a wireless headset that features an additional temperature sensor. The wireless headset is worn on the ear and provides body temperature correction data, enabling the management server to compensate for discrepancies in readings obtained from the smart mask 500. Furthermore, the system may include additional wearable devices such as smart glasses, smart watches, smart healthcare patches, and smart sneakers. The smart glasses provide vision-based information for security personnel, the smart watches offer detailed health monitoring data including heart rate and $SpO_2$ levels, the smart healthcare patches conduct localized skin temperature analysis to improve disease detection accuracy, and the smart sneakers monitor walking patterns to detect abnormal movements indicative of potential health concerns.

The management server of the access management system operates in authenticating the user and ensuring that entry conditions are met. When a user submits an authentication request, the management server receives biometric data from the smart mask 500 and wireless headset, verifies authentication criteria including temperature thresholds, mask-wearing status, and prior health history, and sends an approval message if the user meets the authentication conditions. After entry, the management server continuously monitors biometric data, periodically verifying whether the authentication conditions remain satisfied. If the system detects health abnormalities, it classifies urgency levels into high, medium, or low, issues alerts to the user's guardian or emergency services, and restricts entry if conditions are not met.

To ensure compliance with 35 USC § 101, the present disclosure describes a technological improvement in biometric authentication and airflow control, rather than an abstract idea. The smart mask 500 and fan system 531 represent a specific, tangible device that integrates sensor technology, adaptive airflow management, and real-time feedback mechanisms to achieve a practical application. The management server further enhances technical functionality by implementing real-time biometric analysis, automated decision-making, and IoT-based communication protocols.

What is claimed is:

1. A management server of an access management system configured to determine whether an authentication condition is satisfied when a user wants to enter a management space such that a manager of the access management system approves or rejects the user's authentication request based on the determined authentication condition, the management server comprising:

a memory configured to save commands; and a processor configured to:

receive, from a user terminal associated with the user, an authentication request for the management space of the access management system and the user's biometric data collected by a plurality of smart wearable devices, the plurality of smart wearable devices including a smart mask including a temperature sensor for body temperature measurement, a fan system for air circulation, an external indicator configured to display fan system status, and a wireless headset including an additional temperature sensor formed in a part that is in direct contact with the user's ear;

determine whether the user satisfies the authentication condition of the management space based on the biometric data received from the user terminal and a user's authentication data retrieved from a public database, wherein the satisfied authentication condition allows the user to enter the management space;

send an approval message for the authentication request when the authentication condition is satisfied, and send periodic data requests to the user terminal after the user enters the management space to continuously check whether the authentication condition is satisfied;

periodically receive, from the user terminal, a position of the smart mask and subsequent biometric data of the user generated in response to the periodic data requests from the user terminal, the biometric data and the subsequent biometric data including a body temperature of the user measured by the smart mask worn by the user;

send an authentication failure message to the user terminal if the authentication condition is not satisfied based on the subsequent biometric data and the user's subsequent authentication data periodically received while the smart mask is in the management space, wherein the user is not allowed to enter the management space when the authentication condition is not satisfied;

receive additional biometric data measured by the wireless headset;

control the fan system included in the smart mask based on at least one of the biometric data, the subsequent biometric data, and environmental data received from the management server, wherein the fan system is configured to adjust an airflow rate in response to changes in the user's breathing rate, body temperature, internal humidity of the smart mask, and external air quality data;

provide at least one Internet of Things (IoT) wearable function to the user through the user terminal based on the additional biometric data received from the wireless headset, the at least one IoT wearable function including a body temperature correction function provided through the wireless headset such that the user's body temperature measured by the smart mask is corrected through the additional body temperature data measured by the wireless headset;

calculate a comprehensive health examination score of the user based on the body temperature correction function provided through the wireless headset and the fan system control function provided through the smart mask; and determine whether the user satisfies the authentication condition by additionally considering whether the comprehensive health examination score exceeds a threshold score set according to an age, a gender, and an occupation of the user.

2. The management server of claim 1, wherein, the processor is configured to:

determine whether a health abnormality event has occurred to the user based on the biometric data and the subsequent biometric data; and send a health abnormality notification message to a guardian terminal of the user's guardian registered in advance to the access management system.

3. The management server of claim 2, wherein, the processor, when sending the health abnormality notification message, is configured to:

classify a level of urgency of the health abnormality event into any one of high, medium, and low based on a degree and a number of times that the biometric data and the subsequent biometric data deviate from a health threshold range; and send the authentication failure message in case of low level of urgency, provide an additional emergency call to the guardian terminal in case of medium level of urgency, deliver an additional emergency contact to an emergency protection center in case of high level of urgency.

4. The management server of claim 1, wherein, the biometric data and the subsequent biometric data further comprise the user's body temperature, internal humidity of the smart mask, an airflow rate of the fan system, and whether the smart mask is appropriately worn, measured by the smart mask, wherein, the authentication data and the subsequent authentication data comprise the user's disease infection history, vaccination information, and overseas travel history, wherein the smart mask is a built-in smart mask or an attachable smart mask, which comprises a sensor and a board, a plastic cover, a mask, and the fan system configured to adjust air circulation in response to the biometric and the environmental data, and an external indicator configured to display the fan system status based on the control signals from the processor.

5. The management server of claim 4, wherein, the external indicator displays different colors corresponding to different fan operational states, wherein a first color represents a normal airflow mode, a second color represents an increased airflow mode, and a third color represents a reduced airflow mode.

6. The management server of claim 1, wherein, the at least one additional wearable device further comprises at least one of the wireless headset, smart glasses, a smart watch, a smart healthcare patch, and smart sneakers, wherein the at least one IoT wearable function further includes at least one of the functions including:

the body temperature correction function through the wireless headset, a user vision information provision function provided through the smart glasses, a detailed health data provision function provided through the smart watch, a local area diagnosis function provided through the smart healthcare patch, a behavioral abnormality detection function provided through the smart sneakers, and the fan system control function provided through the smart mask to optimize airflow based on real-time biometric and environmental data, wherein the external indicator provides real-time visual feedback corresponding to the fan system's operational state.

* * * * *